US00PP20843P2

(12) United States Plant Patent
Korlipara

(10) Patent No.: US PP20,843 P2
(45) Date of Patent: Mar. 16, 2010

(54) ***CAMPANULA* PLANT NAMED 'JELLY BELLS'**

(50) Latin Name: *Campanula×pulloides*
Varietal Denomination: Jelly Bells

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/321,473

(22) Filed: Jan. 20, 2009

(51) Int. Cl.
*A01H 5/00* (2006.01)

(52) U.S. Cl. ..... Plt./414

(58) Field of Classification Search ..... Plt./414
See application file for complete search history.

*Primary Examiner*—Annette H Para
(74) *Attorney, Agent, or Firm*—Klarquist Sparkman, LLP

(57) ABSTRACT

A new and distinct *Campanula* plant distinguished by its large nodding bells of deep blue violet flowers and its vigor. Compared to its parent *Campanula×pulloides* 'G. F. Wilson', the new variety has larger flowers, larger leaves, larger plant size, and better vigor.

1 Drawing Sheet

Botanical classification: *Campanula×pulloides*.

Variety denomination: 'Jelly Bells'.

The present invention relates to a new and distinct *Campanula* plant that is given the cultivar name of 'Jelly Bells'. *Campanula* is in the family Campanulaceae. *Campanula* 'Jelly Bells' originated from a branch mutation of *Campanula×pulloides* 'G. F. Wilson' (an unpatented plant).

This new and unique *Campanula* is a mat forming plant distinguished by its large nodding bells of deep blue violet flowers and its vigor. Compared to its parent *Campanula×pulloides* 'G. F. Wilson', the new variety has larger flowers, larger leaves, larger plant size, and better vigor.

This new cultivar has been reproduced only by asexual propagation (tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows *Campanula* 'Jelly Bells' growing in a one gallon container in a sunny greenhouse in June in Canby, Oreg.

DETAILED PLANT DESCRIPTION

The following is a detailed description of the new *Campanula* based on observations of two-year-old-specimens grown in the trial beds outside in full sun under typical weathers in Canby, Oreg. Canby is Zone 8 on the USDA Hardiness map. Temperatures range from a high of 95 degrees F in August to 32 degrees F in January. Normal rainfall in Canby is 42.8 inches per year. The color descriptions are all based on The Royal Horticultural Society Colour Chart.

Plant:

*Form.*—Mat forming herbaceous perennial.
*Hardiness.*—USDA Zone 5–8.

*Size.*—16 cm tall from the ground to the top of the inflorescence and 38 cm wide.
*Habit.*—Low spreading mat with short upright leafy stems.
*Vigor.*—Excellent.
*Roots.*—Main root Grey Brown 199A, side roots Yellow White 158A to 158C;
plants grow easily from divisions.

Stem:

*Size.*—Grows to 15 cm long and 2 mm wide.
*Internode length.*—Grows to 6 mm.
*Surface texture.*—Pubescent.
*Color.*—Yellow Green 147B.

Leaf:

*Type.*—Simple.
*Number.*—Usually 7 leaves per stem.
*Arrangement.*—Alternate.
*Shape.*—Ovate, except upper stem leaves which are lanceolate.
*Venation.*—Pinnate.
*Margins.*—Coarsely serrate.
*Apex.*—Acuminate.
*Base.*—Attenuate.
*Blade size.*—Grows to 25 mm long and 15 mm wide.
*Surface texture.*—Pubescent on both sides.
*Petiole description.*—10 mm to 15 mm long and 1.5 mm wide, pubescent, Yellow Green 146D.
*Leaf color.*—Topside Green 137A, bottom side Yellow Green 147B.

Inflorescence:

*Type.*—Terminal, solitary to 4-branched.
*Peduncle.*—1 cm to 10 cm tall and 1.2 mm wide, pubescent, Yellow Green 146B.
*Pedicel.*—4 cm to 8.5 cm long and 1 mm wide, pubescent, Yellow Green 146B.
*Bloom period.*—May through July with sporatic rebloom in Canby, Oreg.

Flower bud:

*Size.*—6.5 mm wide and 12 mm long.
*Shape.*—Ovoid, elongate, pleated.
*Surface texture.*—Glabrous.
*Color.*—Closest to Violet 90A, but darker.

Flower:

*Type.*—Actinomorphic.

*Shape.*—Campanulate.

*Size.*—Grows to 2 cm long and 1.5 cm wide.

*Corolla.*—1.5 to 2 cm long; with 5 lobes, each 5 mm to 8 mm long and 8 mm wide, triangular, surface texture glabrous inside and out, color outside is Violet Blue 90A with lighter main vein and base White 155A, inside is Violet Blue 90C to 90A at the tips and 85D at the tips.

*Calyx.*—15 mm wide and 8 mm deep, campanulate with long thin flaring lobes, tube 5 mm long and 4 mm wide at lobe junction, lobes are 9 mm long, 2.5 mm wide at the base, entire, acuminate, pubescent outside tube, lobes glabrous, Yellow Green 146A.

*Stamen.*—5, 5 mm long, filaments 1.5 mm long, White 155A, anthers 3.5 mm long and less than 1 mm wide, Yellow White 158A, sterile.

*Pistil.*—1, 15 mm long and 3 mm wide; ovary 4 mm deep and 3 cm wide, Yellow White 145A; style 9.5 cm long and 1 mm wide, White 155A on bottom 2/3 and Greyed Yellow 160B on top 1/3; 3-branched stigma, each reflexed branch 3 mm long and 1 mm wide, Yellow Green 154D.

*Fragrance.*—None.

*Lastingness.*—each flower lasts for about 5 days on the plant.

Fruit and seed: none.

Diseases and pests: No diseases found of this new variety. No known disease resistance. Many *Campanula* sp. are susceptible to snails, slugs, and aphids.

I claim:

1. A new and distinct *Campanula* plant as herein illustrated and described.

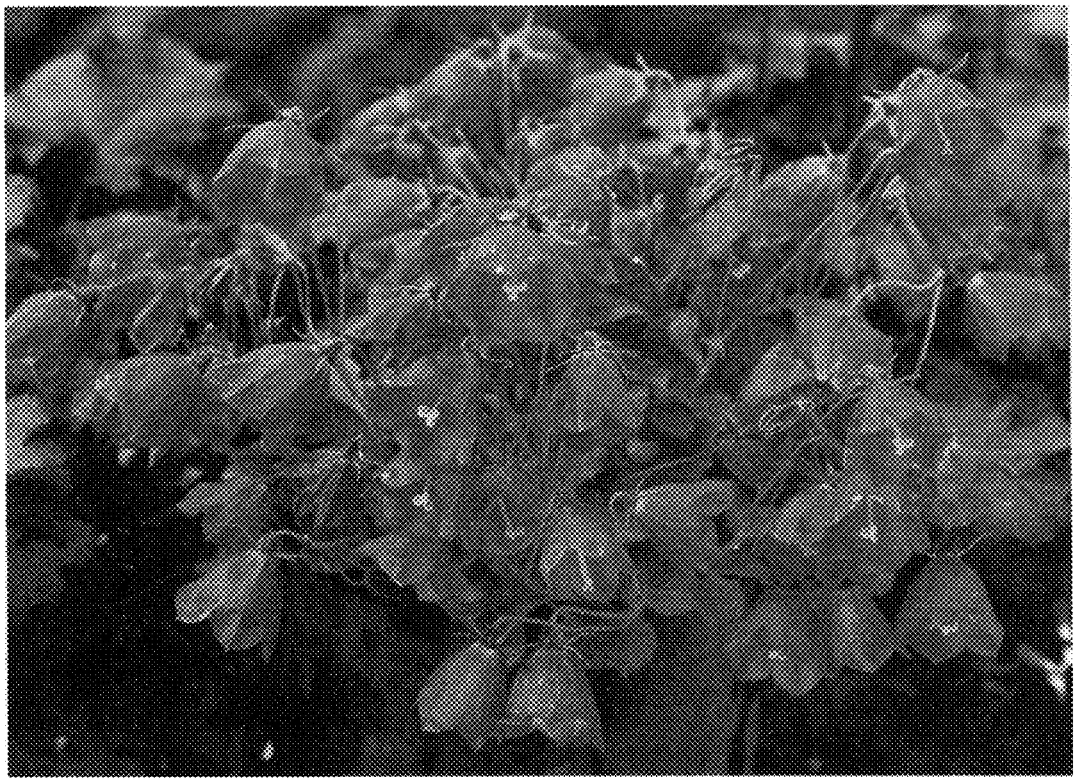

* * * * *